United States Patent [19]

Veinberg et al.

[11] Patent Number: 5,484,936
[45] Date of Patent: Jan. 16, 1996

[54] PROCESSES FOR THE PREPARATION OF 1,3-BIS(1,2,4-TRIAZOL-1-YL)-PROPAN-2-OL DERIVATIVES

[75] Inventors: Alexander Veinberg, Rehovot; Alexander Senderichin, Jerusalem, both of Israel

[73] Assignee: Teva Pharmaceutical Industries Ltd., Jerusalem, Israel

[21] Appl. No.: 217,522

[22] Filed: Mar. 24, 1994

[30] Foreign Application Priority Data

Mar. 29, 1993 [IL] Israel ......................................... 105200

[51] Int. Cl.⁶ ...................... C07D 403/10; C07D 403/02
[52] U.S. Cl. ...................................... 548/265.6; 548/266.6
[58] Field of Search .............................. 548/264.8, 266.6, 548/265.6

[56] References Cited

U.S. PATENT DOCUMENTS 4,404,216   9/1983   Richardson ............................ 424/269

FOREIGN PATENT DOCUMENTS 2051281    3/1993   Canada .
 192962    2/1983   New Zealand .
 208705    9/1985   New Zealand .
2099818   12/1982   United Kingdom .

OTHER PUBLICATIONS

Keay, J. et al., "Regiospecific synthesis of 1-substituted-1,2,4-triazoles using 4-amino-1,2,4-triazole," *Chemical Specialties USA 1991 Symposium*.

Astleford, B. et al., "Synthesis of 1-Alkyl-1,2,4 triazoles: A New One Pot Regiospecific Procedure," *J. Org. Chem.*, vol. 54 (1989), Feb. pp. 731–732.

*Primary Examiner*—Robert Gerstl
*Assistant Examiner*—Laura L. Stockton

[57] ABSTRACT

The invention provides a regiospecific process for the preparation of 1,3-bis(1,2,4-triazol-1-yl)-propan-2-ol derivatives comprising reacting an oxirane acid salt or an oxirane, under acidic conditions, with 4H-4-amino-1,2,4-triazole. The process is particularly useful for preparing fluconazole which is useful in the treatment of fungal infections in animals and humans.

10 Claims, No Drawings

PROCESSES FOR THE PREPARATION OF 1,3-BIS(1,2,4-TRIAZOL-1-YL)-PROPAN-2-OL DERIVATIVES

The present invention relates to a regiospecific process for the preparation of 1,3-bis(1,2,4-triazol-1-yl)-propan-2-ol derivatives.

More particularly, the present invention relates to an improved process for the preparation of 2-(2,4-difluorophenyl)-1,3-bis(1H-1,2,4-triazol-1-yl)propan-2-ol, which is also known by the generic name fluconazole (IV):

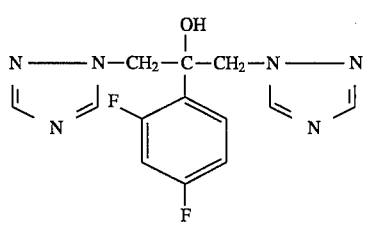

and which is useful in the treatment of fungal infections in animals and in humans.

BACKGROUND OF THE INVENTION AND PRIOR ART

The preparation of fluconazole (IV) by alternative processes has been described in British Patent No. 2,099,818.

A first process involves reacting a compound of the formula V:

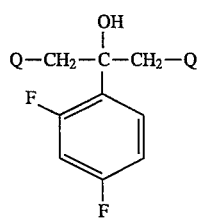

where Q is a facile leaving group, with 1,2,4-triazole wherein Q is Cl or Br.

A second possible process is reacting an oxirane of the formula VI:

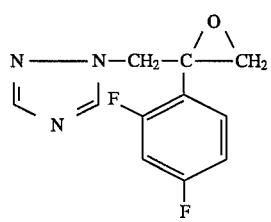

with 1,2,4-triazole.

In both cases, these reactions are not regiospecific and two isomers are observed in the product mixture. In British Patent 2,099,818 it is stated that, "the product will generally be contaminated with the isomer in which one of the triazole rings is attached to the adjacent $CH_2$ via the 4-position." Therefore, the process of British Patent 2,099,818 discloses the need for column chromatography to isolate the desired product from the side product iso-fluconazole.

This lack of regiospecifity in the fluconazole process, as described in British Patent 2,099,818, leads to the following disadvantages: low overall yield; requirement for column chromatography; lack of suitability for usual industrial production conditions, and final product contamination with iso-fluconazole.

In contradistinction to the teachings of said British patent, there has now been surprisingly discovered, according to the present invention, a regiospecific process for the preparation of 1,3-bis(1,2,4-triazol-1-yl)-propan-2-ol derivatives of the general formulas I and Ia:

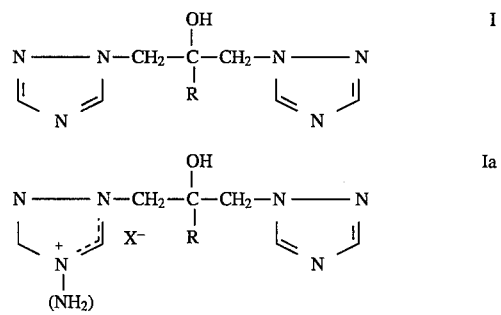

wherein:

R is alkyl, cycloalkyl, aryl or aralkyl optionally substituted by one or more same or different halogen groups; and X is the anion of a strong acid;

comprising reacting an oxirane acid salt of the general formula II:

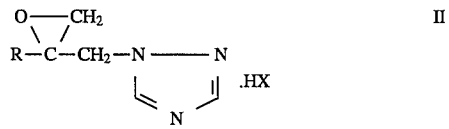

wherein

R and X are as defined above; or reacting an oxirane of the general formula II':

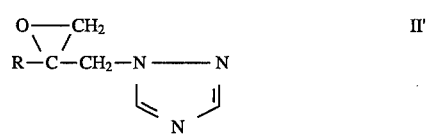

wherein

R and X are as defined above, under acidic conditions, with 4H-4-amino-1,2,4-triazole of the formula III:

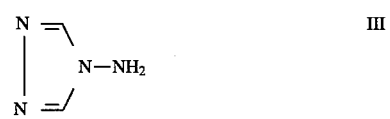

and optionally deaminating a compound of the formula Ia to form a compound of formula I.

In preferred embodiments of the present invention the process will be carried out with an oxirane acid salt of the general formula II as defined above rather than with an oxirane of the general formula II' in the presence of acid.

Preferably X is the anion of a strong acid selected from the group consisting of chloride, sulphate, p-toluenesulphonate and methanesulphonate.

In the process of the present invention the compounds of formula I as defined above are prepared, inter alia, by the deamination of the intermediate compounds of formula Ia as defined above, which intermediate compounds are novel per se and which intermediate compounds have therefore also not been previously taught or suggested for use in the preparation of the compounds of formula I. These novel intermediates can be isolated, if desired, or reacted in situ, as described and exemplified herein, for the preparation of the compounds of formula I.

As will be noted, in the process of the present invention there is used a 4-amino-1,2,4-triazole of formula III, in which the possibility of 4-alkylation is blocked by an amino group.

Bret A. Astleford, et al, *J. Org. Chem.*, Vol. 54, No. 3, p. 731 (1989), describes a synthesis of 1-(2,4 -dichlorophenyl)-2-(1H-1,2,4-triazyl-1-yl)ethanone of the formula VII:

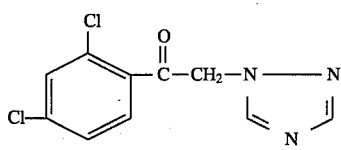

in a regiospecific procedure using 4H-4-amino-1,2,4-triazole (III) in the condensation with 2-chloro-2',4'-dichloroacetophenone of the formula VIII:

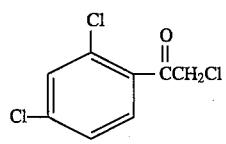

resulting in the isomerically pure hydrochloric salt of IX:

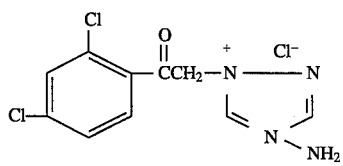

which is then deaminated with sodium nitrate to give the 1-2,4-dichlorophenyl-1-2-(1H-1,2,4-triazol-1-yl)ethanone of formula VII.

As will be noted, however, said Astleford et al reference does not teach the reaction of a 4-amino-1,2,4 -triazole with an oxirane and, as shown in comparative Example A hereinafter, when such a reaction is attempted under the conditions described therein, a complex product mixture is obtained in which fluconazole is only a minor component.

Likewise, when the reaction conditions disclosed in the Example D of the British Patent 2,099,818 are attempted using 4-amino-1,2,4-triazole instead of triazole as described in comparative Example B hereinafter, the desired product was not significantly present in the reaction mixture.

The reactions described in the prior art Astleford, et al. and British Patent 2,099,818 between triazole or aminotriazole and the chloride, or between triazole and the oxirane specify basic reaction conditions. The novel reaction of the present invention between aminotriazole and the oxirane surprisingly requires acidic conditions.

In especially preferred embodiments, said anion of the strong acid is methanesulphonate or p-toluenesulphonate.

The process of the present invention preferably comprises deamination of a compound of formula Ia, to form a compound of formula I and in especially preferred embodiments of the present invention, there is provided a regiospecific process wherein R is 2,4-difluorophenyl, whereby the process provides fluconazole of formula IV.

As will be realized, once fluconazole has been prepared according to the novel process of the present invention, it, or a pharmaceutically acceptable salt thereof, can be used for the preparation of pharmaceutical compositions as taught, e.g., in British Patent 2,099,818, the teachings of which are incorporated herein by reference.

Thus, as known and taught in said patent, the preferred pharmaceutically acceptable salts are the acid addition salts. Pharmaceutically acceptable acid addition salts of the compounds of the formula I are those formed from strong acids, which form non-toxic acid addition salts containing a pharmaceutically-acceptable anion, such as hydrochloride, hydrobromide and sulphate.

The salts may be obtained by conventional procedures, e.g., by mixing solutions containing equimolar amounts of the free base and desired acid, and the required salt is collected by filtration, if insoluble, or by evaporation of the solvent.

Thus the present invention also provides a compound of formula I, or a pharmaceutically acceptable salt thereof, whenever prepared by the process of the present invention, for use in treating fungal infections in humans.

Furthermore, the general principle of the reaction in the process of the present invention between the oxirane or oxirane acid salt and a 4H-4-amino-1,2,4-triazole may be utilized in similar instances where a substituted oxirane or oxirane acid salt is desired to be reacted with a 1,2,4-triazole, i.e., instances where the oxirane is of the formula XI:

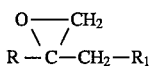

or oxirane acid salt is of the formula XIa:

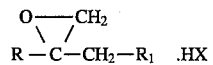

wherein:

R is as defined above, and $R_1$ is hydroxy, halogeno, alkyl, cycloalkyl, aryl, aralkyl or a heterocyclic group, each optionally substituted or unsubstituted.

Thus, the present invention also relates to a regiospecific process for the preparation of 1-(1,2,4 -triazol-1-yl)-propan-2-ol derivatives of the general formulas XII and XIIa:

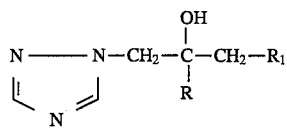

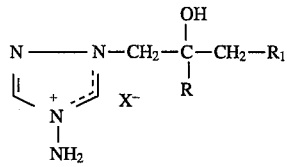

wherein:

R is as defined above;

$R_1$ is hydroxy, halogeno, alkyl, cycloalkyl, aryl, aralkyl or a heterocyclic group, each optionally substituted or unsubstituted, and X is the anion of a strong acid;

comprising reacting an oxirane acid salt of general formula

XIa:

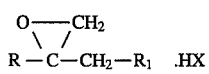 XIa wherein

R, $R_1$ and X are as defined above; or reacting an oxirane of the general formula XI:

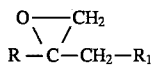 XI wherein

R, $R_1$ and X are as defined above, under acidic conditions, with 4H-4-amino-1,2,4-triazole of the formula III:

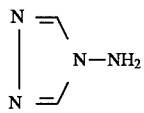 III and optionally deaminating a compound of the formula Ia to form a compound of formula I.

An example of such a reaction, where the above process may be of use, is the one between (R)-(−)-2-(2,4 -difluorophenyl)-2,3-epoxropanol and 1,2,4-triazole described in *Drugs of the Future*, Vol. 18 pp 424–427 (1993), wherein the 1,2,4-triazole may be replaced by a 4H-4-amino-1,2,4-triazole and the conditions outlined in the present application applied, to yield the desired product.

For human use, the anti-fungal compound of the formula I (or salt thereof) can be administered alone, but will generally be administered in admixture with a pharmaceutical carrier selected with regard to the intended route of administration and standard pharmaceutical practice. For example, it may be administered orally in the form of a tablet containing such excipients as starch or lactose, or in a capsule or ovule, either alone or in admixture with excipients, or in the form of an elixir or suspension containing a flavoring or coloring agent. It may be injected parenterally, for example, intravenously, intramuscularly or subcutaneously. For parenteral administration, it is best used in the form of a sterile aqueous solution which may contain other substances, for example, enough salts or glucose to make the solution isotonic.

For oral and parenteral administration to human patients, it is expected that the daily dosage level of the anti-fungal compound of the formula I will be from 0.1 to 5 mg/kg (in divided doses) when administered by either the oral or parenteral route. Thus tablets or capsules of the compounds can be expected to contain from 5 mg to 0.5 g of active compound for administration singly, or two or more at a time, as appropriate. The physician, in any event, will determine the actual dosage which will be most suitable for an individual patient and it will vary with the age, weight and response of the particular patient. The above dosages are exemplary of the average case. There can, of course, be individual instances where higher or lower dosage ranges are merited, and such are within the scope of this invention.

Alternatively, the anti-fungal compound of formula may be administered in the form of a suppository or pessary, or it may be applied topically in the form of a lotion, solution, ointment or dusting powder. For example, it may be incorporated into a ointment consisting of an aqueous emulsion of polyethylene glycols or liquid paraffin, or it may be incorporated, at a concentration, with such stabilizers and preservatives as may be required.

The process of the present invention is preferably carried out in alcohols, water, dimethylsulphoxide, dimethylformamide, acetonitrile, etc., at 50° to 100° C., preferably in boiling 2-propanol followed by deamination with sodium nitrite.

As indicated, R is preferably a halogen-substituted aryl group, and when R is 2,4-difluorophenyl, the product obtained is fluconazole (IV).

According to the method of this invention, IV is isolated in a substantially pure state, without the need for column chromatography. In contrast to British Patent No. 2,099,818, no isomeric side product is observed, even in the crude reaction mixture. The yield of fluconazole is also superior to that disclosed in British Patent 2,099,818.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

Preparation of [2-hydroxy-2-(2',4'-difluorophenyl)-3-(1H-1,2,4-triazol-1-yl)propyl]-1-(4H-1,2,4,-triazolium) methanesulfonate.

A mixture of the oxirane salt of formula II, wherein R is 2,4-difluorophenyl and X is a methanesulfonate anion (4.8 g), 4H-4-amino-1,2,4-triazole (III) (1.5 g) and 2-propanol (500 ml), was heated to reflux for 35 hours. The product was crystallized and then recrystallized from 2-propanol to give 1.35 g (27%) of white crystalline material.

M.p. 98°–101° C.; UV (Ethanol) max 204 nm ($\epsilon$=11,200); max 201 nm ($\epsilon$=645); max 266 nm ($\epsilon$=573).

EXAMPLE 2

Preparation of 2-(2',4'-difluorophenyl)1,3-bis(1,2,4 -triazol-1-yl) -propan-2-ol (Fluconazole) (IV).

A mixture of the oxirane salt of formula II, wherein R is 2,4-difluorophenyl and X is a methanesulfonate anion (167 g), 4H-4-amino-1,2,4-triazole (III) (84 g) and 2-propanol (500 ml) was heated to reflux for 7 hours, whereafter the solvent was evaporated to dryness in vacuo. The residue containing the novel intermediate compound of formula Ia, as defined above, was dissolved in water (2000 ml) and washed with ethylacetate. Concentrated hydrochloric acid (180 ml) was added to a cooled (5° C.) water solution and then sodium nitrite (72.5 g) in water (250 ml) was added dropwise (5°–7° C). The mixture was heated to room temperature; methylene chloride was added, followed by ammonium hydroxide, to pH 8. The methylene chloride layer was separated and the water solution was washed with methylene chloride. The combined methylene chloride solution was washed with ammonium hydroxide (1%) and evaporated to dryness. Chromatographic assay of this methylene chloride solution indicated the presence of 130 g of fluconazole.

The product was further purified by disolution in aqueous hydrochloric acid, and was precipitated by neutralization with ammonium hydroxide. The title compound was recrystallized from isopropanol, to give 93 g of white crystalline material with physical and spectral properties fully consistent with material prepared according to British Patent No. 2,099,818.

Yield: 92.9 g (60.5%). M.p.: 138°–140° C.

EXAMPLE 3

Alternate Preparation of Fluconazole

A mixture of the oxirane of formula II' (410 mg), where R is 2,4-difluorophenyl, 4H-4-amino-1,2,4-triazole (284 mg), methanesulfonic acid (190 mg) in 2-propanol (1.5 mL) was heated to reflux for 4 hrs, after which the solvent was evaporated in vacuo. The residue was dissolved in water (6 mL), cooled at 5° and concentrated hydrochloric acid (1 mL) was added, followed by a solution of sodium nitrite (300 mg) in water (2 mL, dropwise). The resulting solution was allowed to warm to room temperature, methylene chloride (6 mL) was added, the pH adjusted to 10 with ammonium hydroxide, and the phases separated.

The substantial presence of fluconazole in the organic phase was demonstrated by chromatographic means; however, the reaction mixture was more complex than that obtained by the preferred method of Example 2.

COMPARATIVE EXAMPLE A

Attempted Preparation of Fluconazole

A mixture of oxirane of formula II', where R is 2,4-difluorophenyl (500 mg) and n is 0, 4H-4-amino-1,2,4-triazole (176 mg) and 2-propanol (4 mL) was heated to reflux for 4 hrs. Following the solvent removal in vacuo the residue was dissolved in water (6 mL), cooled and concentrated hydrochloric acid (1.5 mL) was added, followed by a solution of sodium nitrite (300 mg) in water (2 mL dropwise). The resulting solution was allowed to warm to room temperature, methylene chloride (6 mL) was added, the pH of the mixture was adjusted to 10 with ammonium hydroxide, and the phases were separated.

Chromatographic analysis of the organic phase revealed a complex product mixture in which fluconazole was only a minor component.

COMPARATIVE EXAMPLE B

Attempted Preparation of Fluconazole

A mixture of the oxirane salt of formula II (1.68 g), where R is 2,4-difluorophenyl, and X is methanesulfonate anion, 4H-4-amino-1,2,4-triazol (840 mg) anhydrous potassium carbonate (2.27 g) in dimethylformamide (9 mL) was heated to 90° for 4.5 hrs, at which time it was cooled to 5° and concentrated hydrochloric acid (4 mL) was added. A solution of sodium nitrite (700 mg) in water (6 mL) was added dropwise, and the resulting solution allowed to warm to room temperature. Methylene chloride (12 mL) was added, the pH of the mixture adjusted to 10 with ammonium hydroxide, and the phases were separated.

Chromatographic analysis of the organic phase revealed a complex product mixture that did not contain fluconazole.

COMPARATIVE EXAMPLE C

Attempted Preparation of Fluconazole

A suspension of epoxide salt II (50 mg,) aminotriazole V (25 mg) potassium carbonate (69 mg) in acetonitrile (3 mL) was heated to reflux for 21 hrs. Chromatographic examination of the reaction mixture indicated the presence only of starting materials.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A regiospecific process for the preparation of 1,3-bis(1, 2,4-triazol-1-yl)-propan-2-ol derivatives of the general formulas I and Ia:

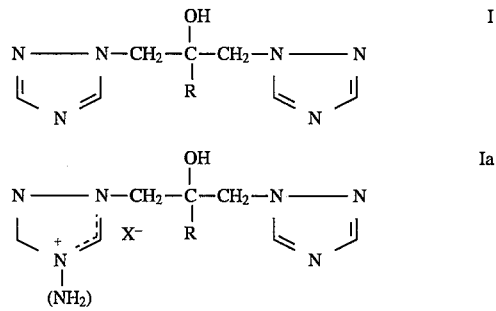

wherein:

R is alkyl, cycloalkyl, aryl or aralkyl optionally substituted by one or more same or different halogen groups; and X is the anion of a strong acid, comprising reacting an oxirane acid salt of the general formula II:

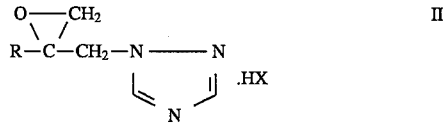

wherein

R and X are as defined above; or reacting an oxirane of the general formula II':

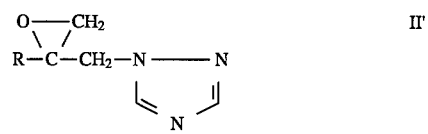

wherein

R and X are as defined above, under acidic conditions, with 4H-4-amino-1,2,4-triazole of the formula III:

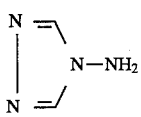

and optionally deaminating a compound of the formula Ia to form a compound of formula I.

2. A regiospecific process according to claim 1, for the preparation of 1,3-bis(1,2,4-triazol-1-yl)-propan-2-ol derivatives of the general formulas I and Ia:

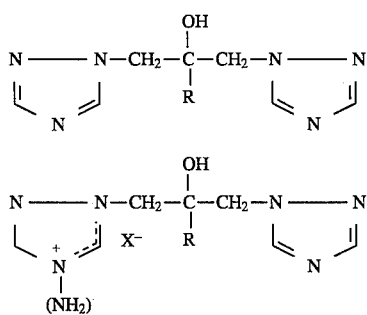

wherein:

R is alkyl, cycloalkyl, aryl or aralkyl optionally substituted by one or more same or different halogen groups; and X is the anion of a strong acid comprising reacting an oxirane acid salt of the general formula II:

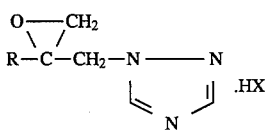

wherein

R and X are as defined above;
under acidic conditions, with 4H-4-amino-1,2,4-triazole of the formula III:

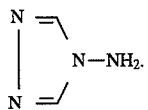

3. A regiospecific process according to claim 1, wherein R is a halogen substituted aryl group.

4. A regiospecific process according to claim 3, wherein R is 2,4-difluorophenyl.

5. A regiospecific process according to claim 1, wherein X is the anion of a strong acid selected from the group consisting of chloride, sulphate, p-toluenesulphonate and methanesulphonate.

6. A process according to claim 5, wherein the anion of the strong acid is methanesulphonate.

7. A process according to claim 5, wherein the anion of the strong acid is p-toluenesulphonate.

8. A process according to claim 1, comprising deamination of a compound of formula Ia, to form a compound of the formula I.

9. A process according to claim 1, comprising reacting an oxirane of the general formula II as defined, with 4H-4-amino-1,2,4-triazole in the presence of at least one equivalent weight of acid per mole of oxirane.

10. A regiospecific process for the preparation of 1-(1,2,4-triazol-1-yl)-propan-2-ol derivatives of the general formulas XII and XIIa:

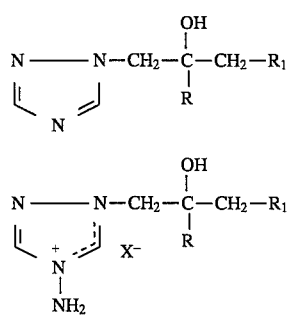

wherein:

R is alkyl, cycloalkyl, aryl or aralkyl optionally substituted by one or more same or different halogen groups;

$R_1$ is hydroxy, halogeno, alkyl, cycloalkyl, aryl, aralkyl or a heterocyclic group, each optionally substituted or unsubstituted, and X is the anion of a strong acid;
comprising reacting an oxirane acid salt of the general formula XIa:

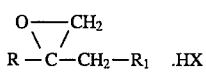

wherein

R, $R_1$ and X are as defined above; or reacting an oxirane of the general formula XI:

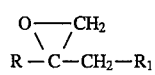

wherein

R, $R_1$ and X are as defined above, under acidic conditions, with 4H-4-amino-1,2,4-triazole of the formula III:

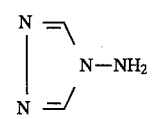

and optionally deaminating a compound of the formula Ia to form a compound of formula I.

* * * * *

UNITED STATES PATENT AND TRADEMARK OFFICE
CERTIFICATE OF CORRECTION

PATENT NO. : 5,484,936

DATED : JANUARY 16, 1996

INVENTOR(S) : VEINBERG, A. et al.

It is certified that error appears in the above-indentified patent and that said Letters Patent is hereby corrected as shown below:

In column 6, line 36, Example 1, change "(4H-1 2, 4, -triazolium)" to --(4H-4-amino-1, 2, 4, -triazolium)--.

In column 7, line 3, change "disolution" to --dissolution--.

In column 8, line 4, change "aminotriazole V" to --aminotriazole III--.

In column 10, lines 56-57, claim 10, change "formula Ia to form a compound of formula I" to --formula XIIa to form a compound of formula XII--.

Signed and Sealed this

Fifteenth Day of July, 1997

Attest:

BRUCE LEHMAN

Attesting Officer

Commissioner of Patents and Trademarks